United States Patent
Cropper

(10) Patent No.: US 7,115,105 B2
(45) Date of Patent: Oct. 3, 2006

(54) ANKLE CONTROL SYSTEM

(76) Inventor: Dean E. Cropper, 240 E. Hersey St., Suite 2, Ashland, OR (US) 97520

( * ) Notice: Subject to any disclaimer, the term of this patent is extended or adjusted under 35 U.S.C. 154(b) by 511 days.

(21) Appl. No.: 10/133,636

(22) Filed: Apr. 29, 2002

(65) Prior Publication Data

US 2003/0204157 A1 Oct. 30, 2003

(51) Int. Cl.
*A61F 13/00* (2006.01)
(52) U.S. Cl. .......................... 602/27; 602/65
(58) Field of Classification Search .................. 602/27, 602/65, 23, 26, 28, 29, 60; 128/882
See application file for complete search history.

(56) References Cited

U.S. PATENT DOCUMENTS

| | | | | |
|---|---|---|---|---|
| 2,800,900 A | * | 7/1957 | Schultz | 602/27 |
| 4,085,746 A | * | 4/1978 | Castiglia | 602/65 |
| 4,280,488 A | | 7/1981 | Polsky et al. | |
| 4,280,489 A | * | 7/1981 | Johnson, Jr. | 602/27 |
| 4,313,433 A | * | 2/1982 | Cramer | 602/27 |
| 4,323,058 A | | 4/1982 | Detty | |
| 4,367,733 A | * | 1/1983 | Stromgren | 602/65 |
| 4,590,932 A | * | 5/1986 | Wilkerson | 602/65 |
| 4,597,395 A | | 7/1986 | Barlow et al. | |
| 4,621,648 A | | 11/1986 | Ivany | |
| 4,628,945 A | * | 12/1986 | Johnson, Jr. | 602/27 |
| 4,640,025 A | | 2/1987 | DeRenzo | |
| 4,651,726 A | | 3/1987 | Holland | |
| 4,724,847 A | * | 2/1988 | Nelson | 602/27 |
| 4,729,370 A | * | 3/1988 | Kallassy | 602/65 |
| 4,844,058 A | * | 7/1989 | Vogelbach | 602/27 |
| 4,878,504 A | | 11/1989 | Nelson | |
| 5,050,620 A | * | 9/1991 | Cooper | 602/27 |
| 5,067,486 A | | 11/1991 | Hely | |
| 5,099,860 A | * | 3/1992 | Amrein | 128/882 |
| 5,125,400 A | | 6/1992 | Johnson, Jr. | |
| 5,330,419 A | * | 7/1994 | Toronto et al. | 602/27 |
| 5,620,413 A | * | 4/1997 | Olson | 602/65 |
| 5,735,807 A | * | 4/1998 | Cropper | 602/63 |
| 5,755,679 A | * | 5/1998 | Selner et al. | 602/27 |
| 5,795,316 A | * | 8/1998 | Gaylord | 602/27 |
| 5,899,872 A | * | 5/1999 | Gilmour | 602/65 |
| 6,109,267 A | * | 8/2000 | Shaw et al. | 128/882 |
| 6,117,098 A | * | 9/2000 | Weber et al. | 602/27 |

* cited by examiner

*Primary Examiner*—Michael A. Brown
*Assistant Examiner*—Huong Q. Pham
(74) *Attorney, Agent, or Firm*—The Harris Firm

(57) ABSTRACT

An ankle control system, having a form-fitting sock, a semi-rigid support member, a lever motion stabilizing strap, a stirrup strap, and collar. The form-fitting sock has opposing medial and lateral sides, a foot portion having an arch portion, and an ankle portion having a vertical Achilles tendon portion. The semi-rigid support member is connected to the sock and has at least one slot providing flexibility to contour over an ankle as pressure is exerted on the support member. The lever motion stabilizing strap acts as a lasso to restrict inversion, eversion, and plantar flexion/inversion through the lever action of the foot with respect to the ankle. The stirrup strap is adjustably attachable to the sock.

21 Claims, 6 Drawing Sheets

ANKLE CONTROL SYSTEM

BACKGROUND OF THE INVENTION

The present invention relates to an ankle control system and more particularly, to an ankle control system, which provides superior yet comfortable support while allowing a full range of movement required for walking, running, and jumping. The present invention also relates to a method for controlling an ankle.

Ankle sprains, contusions, arthritis, and tendonitis are common occurrences. For example, one of the most common causes for sprains are overextension of an ankle during athletic activity. Of course, numerous other situations exist where ankle injury is sustained. As such, for athletes and non-athletes alike, a need exists for an effective, comfortable ankle support, both to prevent and to help remedy these various ankle injuries. There are three common types of sprains—1) inversion, whereby the foot folds inwardly, 2) eversion, whereby the foot folds outwardly, and 3) plantar flexion/inversion, whereby the foot folds both inwardly and downwardly. The first and third of these types of injuries is made particularly painful because of damage to the ligament controlling the lever motion of the foot with respect to the ankle, which occurs during plantar-flexion and dorsi-flexion, the two movements necessary for walking, running, and jumping.

Certain types of sprains are further characterized as "high," depending on the ligament or ligaments affected. Individual ankles and types of sprains vary and must be treated and prevented accordingly to achieve a desired effect, which depends on the relative positioning of the support applied. For example, many sprains often affect multiple ligaments, and thus call for support accounting for each affected ligament. For example, during treatment once one ligament has healed, efforts to remedy a sprain should be focused on supporting any other ligament still affected. Moreover, individual ankle sizes and shapes vary from individual-to-individual and therefore respond differently to various positioning of support.

Heretofore several attempts have be made to provide adequate and comfortable support to remedy or prevent these types of injuries.

For example, U.S. Pat. No. 5,067,486 issued to Hely ("Hely") relates to a boot-like body member having a pair of stabilizing straps both fixedly attached at the rear of an ankle in one particular, immovable position. This configuration does not allow for adjustable positioning of these straps in accordance with various types of sprains, and further requires two straps, which do not tighten as effectively as a single strap around the rear portion of the boot. Hely fails to account for the various positions of sprains along the vertical length of the ankle, and includes no mechanism directed to controlling foot-ankle lever motion.

U.S. Pat. No. 4,729,370 issued to Kallassy ("Kallassy") relates to an ankle support having a lateral strap, a medial strap, and a lateral strap. Kallassy also fails to provide adjustable positioning accounting for the height of a sprain, and is ineffective in providing lever motion control. Kallassy's lateral strap is attached only to the lateral side of the ankle. Kallassy therefore does not provide an effective way of controlling the lever motion of the foot.

It is therefore an object of the present invention to remedy the defects of prior ankle control systems, and, in particular, to provide an ankle control system that is lightweight, easy to wear and effective when worn in any type of shoe.

An additional object of the present invention is to provide an ankle control system that affords control over the lever action, i.e., lever motion, of a foot to remedy and prevent plantar flexion/inversion.

Yet a further object of the present invention is to provide an ankle control system that flexes to conform to the malleolus while providing rigid support.

SUMMARY OF THE INVENTION

In accordance with the above objects, the present invention provides an ankle control system, comprising: a form fitting sock, a semi-rigid support member, a lever motion stabilizing strap, and a stirrup strap. The form-fitting sock has opposing medial and lateral sides, a foot portion having an arch portion, and an ankle portion having a vertical Achilles tendon portion. The semi-rigid support member is connected to the sock and has at least one slot providing flexibility to contour over an ankle as pressure is exerted on the support member. In a preferred embodiment, the support member has a plurality of slots. The lever motion stabilizing strap has a first end removably attachable to the foot portion of the sock. The stabilizing strap is wrapable around the foot portion to securely attach to the first end, and has a second end adjustably attachable to one of the lateral and medial sides. The stirrup strap is adjustably attachable to the sock along the vertical portion and has a first end sequentially wrapable from the vertical portion, around a first side, over the arch portion to an opposing second side, and under the foot portion to allow adjustable attachment to the sock on the first side.

According to one preferred embodiment of the invention, the stirrup strap has a second end sequentially wrapable from the vertical portion, around the second side, over the arch portion to the first side, and under the foot portion to allow adjustable attachment to the second side.

According to a still further embodiment, the system further comprises an elastic collar securing the first end of the stirrup strap and second end of the stabilizing strap to the sock.

According to yet another embodiment of the invention, the sock comprises a laminate material no greater than about 0.025" to 0.045" thickness and comprising a polyurethane membrane no greater than about 0.001" thickness and a stretchable material covering the membrane. The material, in a stretched state, has the property of low active compressibility force and strong passive resistance to expansion substantially greater than the compressibility force.

According to a still further embodiment, the lever motion stabilizing strap and the stirrup strap are attachable to the sock by a hook and loop material.

According to yet another embodiment, the first end of the stabilizing strap comprises either hook or loop material on one side for attachment to the sock member, and either hook or loop material on a second side for attachment to a mid-portion of the stabilizing strap once the strap is wrapped around the foot portion.

According to still further embodiments, the stirrup strap and stabilizing strap are provided with pull-loops for quick and easy adjustment.

According to yet a further embodiment, the system further comprises a second semi-rigid support member connected to the sock and having at least one slot providing flexibility to contour over an ankle as pressure is exerted on the support member, wherein one support member is connected to one side of the sock and the second support member is connected to the other side of the sock.

According to yet another embodiment, the at least one slot is open-ended.

In accordance with a still further embodiment of the invention, there is provided a method of controlling an ankle. The first step of the method comprises providing (1) a form-fitting sock having opposing medial and lateral sides, a foot portion having an arch portion, and an ankle portion having a vertical Achilles heel portion, (2) a semi-rigid support member connected to the sock and having at least one slot providing flexibility to contour over an ankle as pressure is exerted on the support member, (3) a lever motion stabilizing strap, and (4) a stirrup strap. The second step comprises fitting the sock onto a foot. The third step comprises attaching a first end of the lever motion stabilizing strap to the foot portion of the sock, wrapping the stabilizing strap around the foot portion to securely attach an intermediate portion of the stabilizing strap to the first end of the stabilizing strap, and adjustably attaching a second end of the stabilizing strap to the lateral side. The fourth step comprises adjustably attaching a stirrup strap to the sock along the vertical portion and sequentially wrapping a first end of the stirrup strap from the vertical portion, around the medial side, over the arch portion to the opposing lateral side portion, and under the foot portion, and adjustably attaching the first end to the sock on the medial side.

A further embodiment of the method according to the invention comprises the additional step of sequentially wrapping a second end of the stirrup strap from the vertical portion, around the lateral side, over the arch portion to the opposing medial side portion, and under the foot portion, and adjustably attaching the first end to the sock on the lateral side.

In a still further embodiment of the method, the support member comprises a plurality of slots.

In yet another embodiment of the method, the step of providing comprises providing a second semi-rigid support member connected to the sock and having at least one slot providing flexibility to contour over an ankle as pressure is exerted on the support member, wherein the first support member is connected to the lateral side of the sock, and the second support member is connected to the medial side of the sock.

Further objects, features and advantages of the present invention will become apparent from the Detailed Description of Preferred Embodiments, which follows, when considered together with the attached Figures.

DETAILED DESCRIPTION

Figure 1:
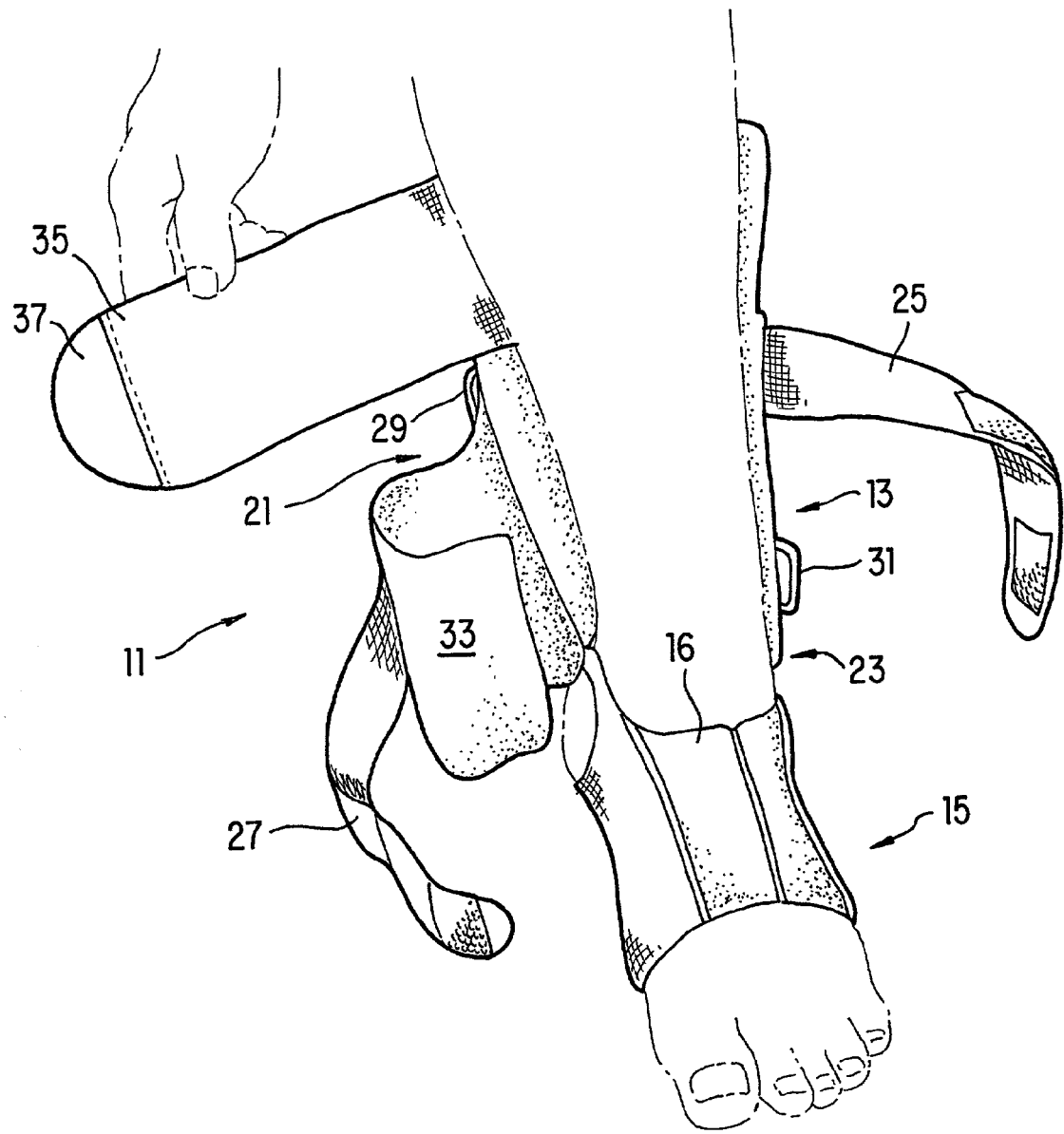
FIG. 1 is a right side perspective view of an ankle control system according to an embodiment of the present invention showing an open sock with a collar in an "up" position, being worn on a left foot.
Figure 5:
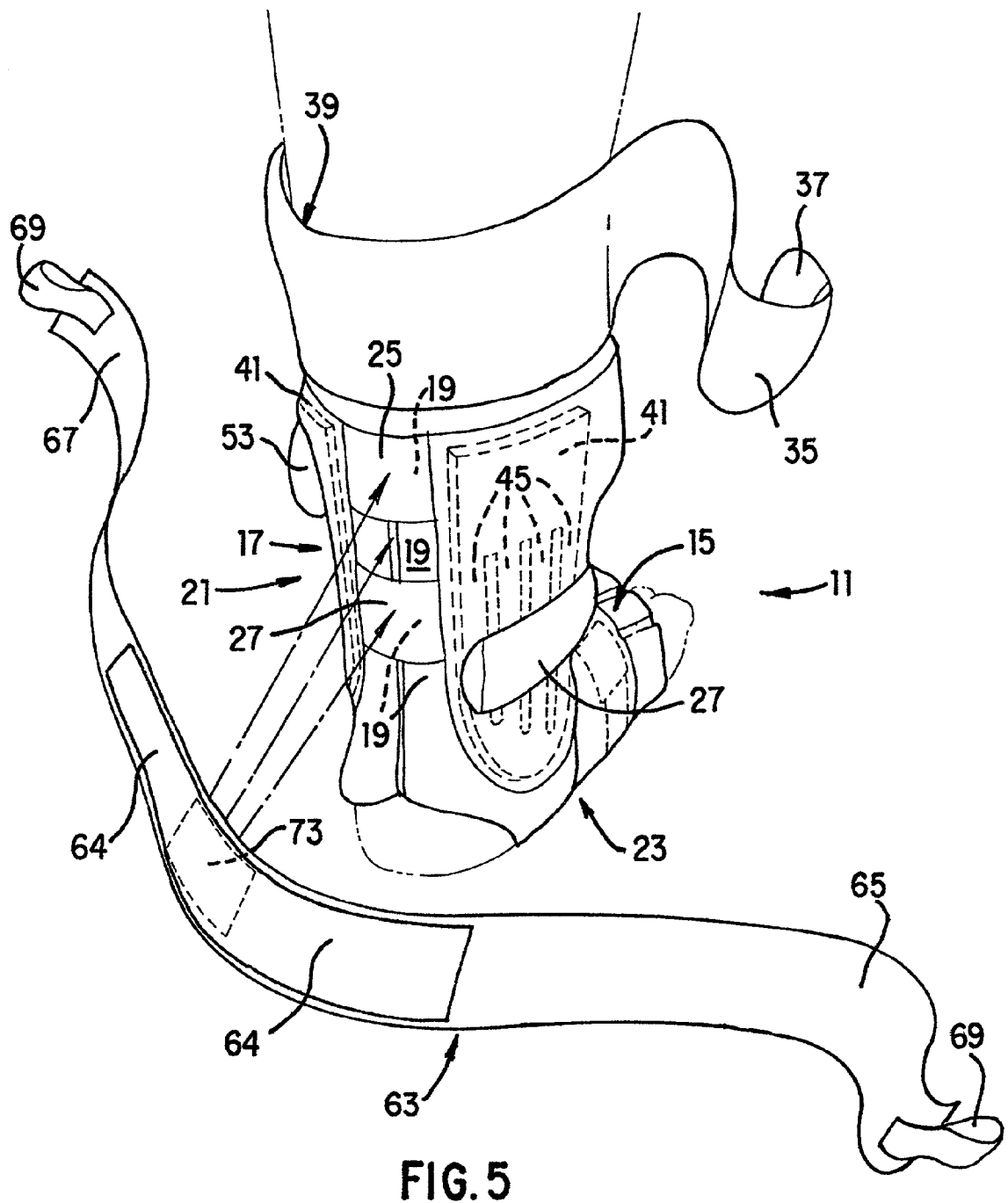
FIG. 5 is an exploded rear perspective view of the sock and attached stabilizing strap shown in FIG. 4 with a stirrup strap according to an embodiment of the present invention.

In accordance with the present invention, FIG. 1 shows a form-fitting sock 11 having a open-faced ankle portion 13, and stretchable foot portion 15, having an arch portion 16. The sock 11 has opposing medial 21 and lateral 23 sides, named as such in accordance with the medial and lateral sides of the ankle and lower leg of the person wearing the sock 11—this designation depends on whether the sock is worn on the right or left foot. As seen in FIG. 5, this sock 11 also has a rear portion 17, which includes a vertical portion 19 along the Achilles tendon of the person wearing the sock 11. Referring again to FIG. 1, a padded barrier, preferably comprising a two-sided fleece barrier 33 also is fixed, and preferably sewn, to one side of the ankle portion 13 of the sock 11 but is not attached to the opposing (here in FIG. 1, lateral) side of the sock. This barrier 33 folds over the wearer's foot under the closure straps 25 and 27 when worn. The barrier 33 as described allows both easy access and added breathability, moisture wicking, and padding for comfort to the front of the wearer's ankle and lower leg. Finally, the sock has an elastic collar 35, which is shown in an "up" position in FIG. 1.

The foot portion 15 of the sock 11 may be constructed from any material suitable for use while wearing a shoe, including any thin elastic material. In a preferred embodiment, the foot portion 15 and ankle portion 13 of sock 11 are primarily made from a thin, highly elastic material of the type disclosed in U.S. Pat. No. 5,735,807 issued to Cropper, which is hereby incorporated by reference in its entirety. In particular, this material comprises a laminate material no greater than about 0.025 to 0.045 inch thickness and comprised of a polyurethane membrane no greater than about 0.001 inch thickness and a stretchable material covering said membrane, said material in a stretched state having the property of low active compressibility force and strong passive resistance to expansion substantially greater than the compressibility force. The exterior surface of the sock 11 is made of a stretchable material, which is compatible for strap attachment with straps having hooks for a hook-and-loop-type attachment.

After the wearer inserts his or her foot into the foot portion 15, the sock 11 can be closed by feeding opposing closure straps 25 and 27 (in an alternate preferred embodiment lower closure strap 27 is elastic) through respective opposing buckles 29 and 31 and folding the straps 25 and 27 back onto themselves at a desired tightness to affix the sock 11 to the wearer's foot through a hook and loop fastening system. Specifically, the sides of these straps have opposing hooks and loops to engage each other. The ends of the inelastic closure straps 25 and 27 feed through the buckles 29 and 31 and attach back onto themselves. There is enough hook material attached to the underside of strap 25 and 27 to securely attach to the straps over sock 11. The top closure strap 25 and bottom closure strap 27 are circumferential straps sewn down to the sock 11 to provide secure attachment positions for the lever motion stabilizing strap 49 and stirrup strap 63. The straps 25 and 27 are shown fastened in FIG. 4.

Figure 2C:
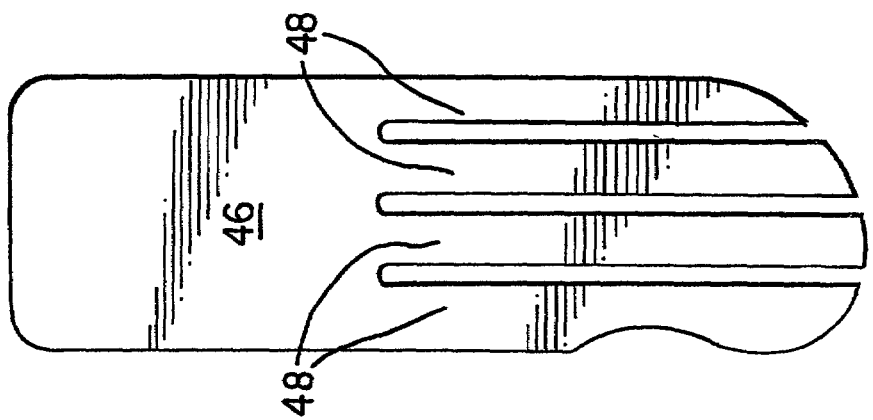
FIG. 2c is a plan view of a third preferred embodiment of a support member according to the present invention.
Figure 2B:
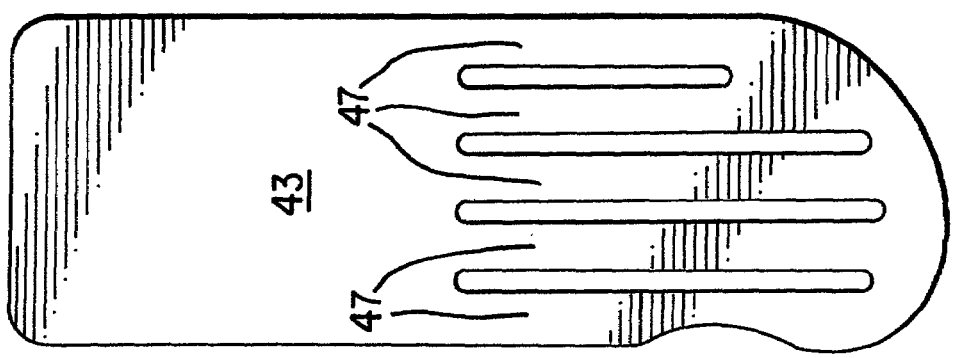
FIG. 2b is a plan view of a second preferred embodiment of a support member according to the present invention.
Figure 2A:
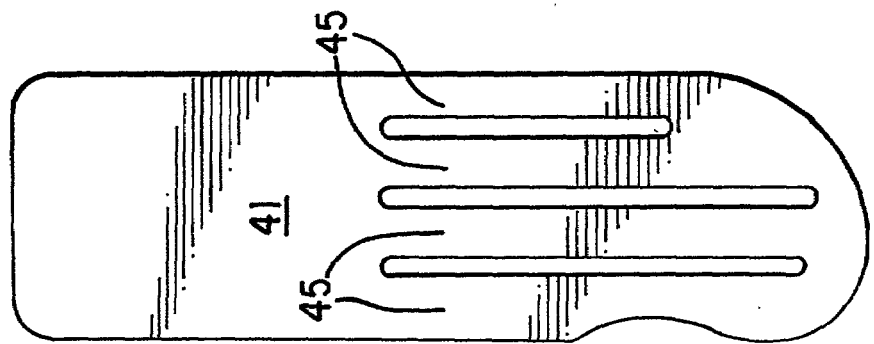
FIG. 2a is a plan view of a first preferred embodiment of a support member according to the present invention.

FIGS. 2A and 2B show two embodiments of slotted support members according to the present invention. These semi-rigid support members each have one or more slots, in this embodiment, three and four, respectively, defining slats 45, 47, which resiliently buckle away from the plane defined by the support members 41, 43 when pressure is applied thereon. The support members are made from a thin resilient material, which is preferably a plastic like polycarbonate plastic, or any other suitable semi-rigid material. Support members, 41, 43 are preferably about 2.0 mm, or about 1/16" thick. The slots are cut into the resilient material so as to conform to the protruding shape of the medial and lateral malleolus to provide a contoured fit, as well as comfort and support through a full range of plantar-flexion and dorsi-flexion motions.

As depicted in FIG. 5, a small support member 41 is sewn inside each of the medial side 21 and the lateral side 23 of the ankle portion 13 of the sock 11 and forcibly strapped against the malleolus of the wearer. Support members 41 are covered with a loop material on respective medial side 21 and lateral side 23 to allow attachment of straps 49 and 63. (See FIG. 5). Upon application of force from straps 25 and 27, the slats 45 buckle to conform to the malleolus. The support member 41 thus provides resilient support to the ankle and contouring over malleolus as pressure is exerted on the support member. For larger feet, a pair of support members 43 as shown in FIG. 2 may be used, whereby slats 47 similarly bend upon the application of force. The support members 41 in FIG. 5 are preferably positioned so that they rest at an angle against a portion of the medial and lateral malleolus, and preferably parallel to the wearer's foot. Various injuries, however, may call for positioning of the support members 41 at a more rear or forward position with respect to the malleolus.

In an alternate preferred embodiment seen in FIG. 2c, the support member 46 (or support members) comprises multiple, flexible, open-ended slots, which define finger-like structures 48 made of a similar material, which also conform to the protruding shape of the medial and/or lateral malleolus to provide a contoured fit.

Figure 3:
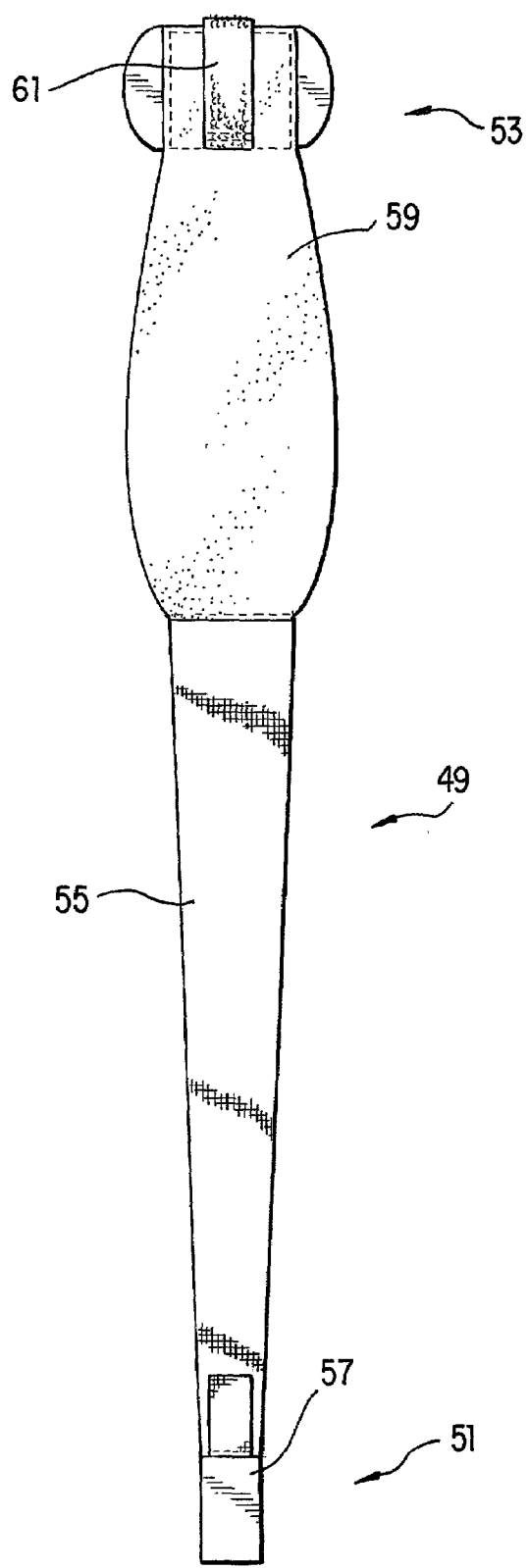
FIG. 3 is a plan view of the top side of a lever motion stabilizing strap according to an embodiment of the present invention.

FIG. 3 shows the top side of a lever motion stabilizing strap 49 having a tapered first end 51 and a wider second end 53, both of which attach to the sock 11 by a hook and loop system. The under side of end 53 and both sides of end 51 have hook material. The top side 59 of wider end 53 has loop (also known as pile) material. Strap 49 is made from an inelastic material, preferably a polyamide (nylon), but can be of any inelastic material suitable for restraining the lever motion of a foot with respect to the ankle.

Figure 4:
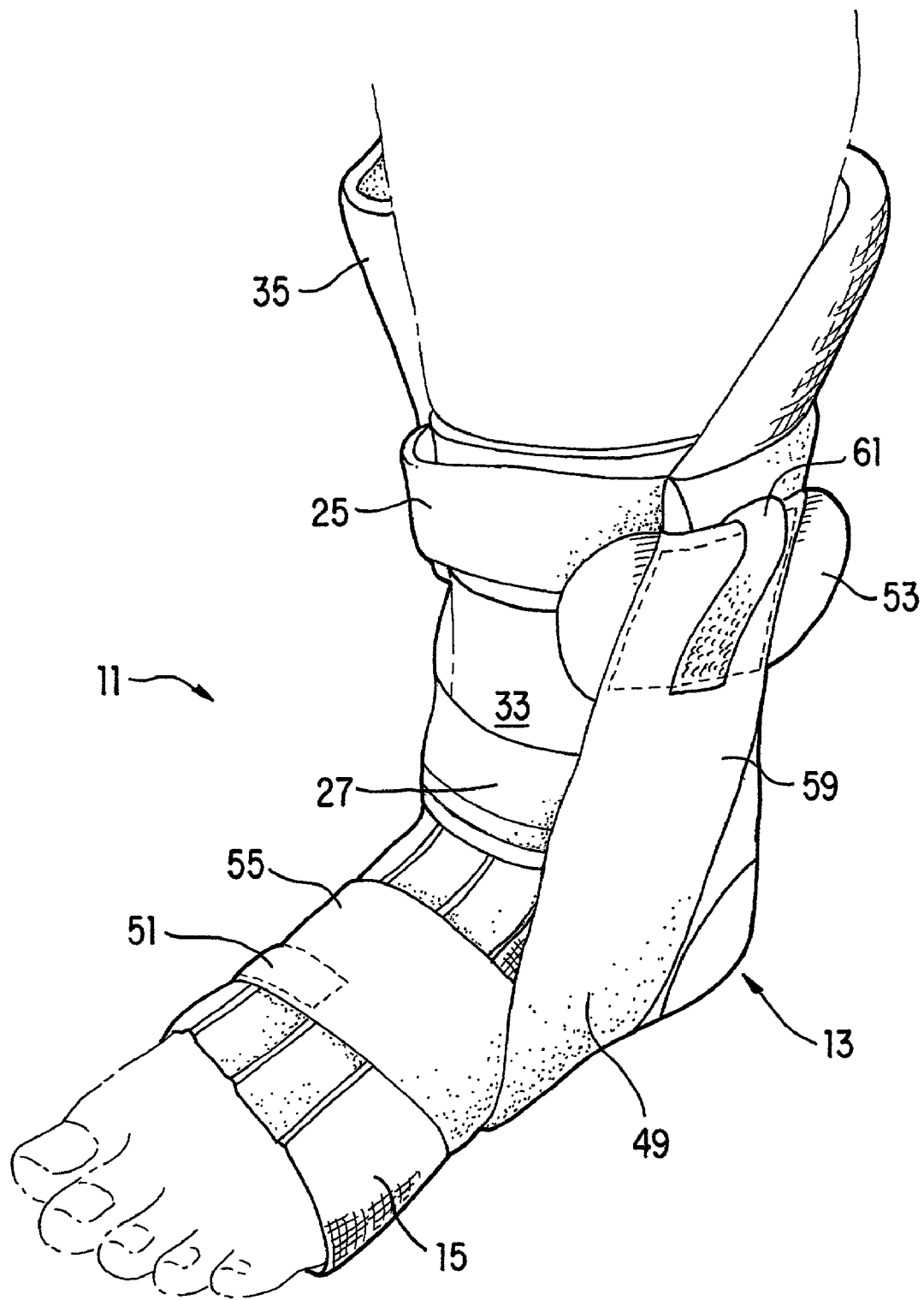
FIG. 4 is a left side perspective view of the sock shown in FIG. 1 in a closed position but having the collar in an "up" position, and including the lever motion stabilizing strap of FIG. 3 attached in accordance with an embodiment of the present invention.

As seen in FIG. 4, after the sock 11 is attached by straps 25, 27, a lever motion stabilizing strap 49 is removably attached to the foot portion 15 of the sock 11. This strap 49 wraps circumferentially around the foot portion 15 and over an exposed side of the first end 51. Pile on an underside (not shown) of the middle portion 55 contacts hooks on top side 57 of first end 51 and becomes secured thereto. This forms a circumferential restraint around the entire foot portion 15, which allows effective lever motion control of the wearer's foot. The loop thereby created, coupled with the attached remaining end of strap 49, acts as a lasso to restrict plantar flexion/inversion through the lever action of the foot with respect to the ankle. Using finger loop 61, strap 49 is tightened and adjusted as needed. According to the sufficient and appropriate tightness to produce the desired control, second end 53 is adjustably attached along lateral side 13 of sock 11 through a hook and loop system. In addition, the strap 49 is hook and loop compatible and is specifically attached to a distal end of medial side 21 of the foot portion 15 via a hook and loop fastener. Strap 49 and finger loops 69 have exterior loop material to improve the attachment of the hook material on strap 63, infra. The strap 49 is long enough to wrap around the foot to the point of initial attachment. In a preferred embodiment, the strap 49 attaches to itself by a fastener, in this embodiment, a hook and loop fastener, between separate portions of the strap 49, and again passes under the foot and attaches to the lateral side of the ankle (i.e., the lateral side 23 of sock 11, and/or closure straps 25 and 27, depending upon the relative size of the wearer's foot and the fit of the sock 11), via a hook tab, attached on the second end 53 of strap 49.

In an alternate preferred embodiment (not shown), strap 49 is attached to the medial side but in a likewise circumferential fashion around the distal end of the foot portion 15 with initial attachment on the lateral side 23, to remedy and prevent eversion. In yet another alternate preferred embodiment two straps 49 can be used in this fashion, one on each side of the foot.

As seen in FIG. 5, inelastic stirrup strap 63 is adjustably and removably attached to sock 11 along vertical portion 19. It is variously attachable along the vertical length of the Achilles tendon according to the positioning and type (e.g., high or low) of sprain sustained or protection required. Specifically, strap 63 is variously attached by hook material on tab 73 to loop material on closure straps 25, 27, to the exposed vertical portion 19 of sock 11, or to some combination thereof. Strap 63 has a first end 65, which beginning from the vertical portion 19, is sequentially wrapped around the medial side 23, over the arch portion 16 to opposing lateral side portion 21, and under foot portion 15 to allow adjustable attachment to the sock on medial side 23. This controls the wearer's foot to prevent eversion.

The stirrup strap 63 also has a second end 67 sequentially wrapable from the vertical portion 19, around the lateral side 21, over the arch portion 16 to the opposing medial side 23, and under the foot portion 15 to allow adjustable attachment to the sock 11 on its lateral side 21. This controls the wearer's foot to prevent inversion. Both first end 65 and second end 67 have finger loops 69 to allow easy tightening and adjustment of stirrup strap 63, as needed. A patch 64 of loop material is sewn on both middle portions of strap 63 to promote attachment of the ends 65 and 67, each of which have hook material on their undersides. Thus, stirrup strap 63 having finger pull loops 69 is connected to the rear portion 17 of the sock 11 and/or the closure straps 27 and 25 and is adjustable along the back of the sock 11 over the Achilles tendon. This strap 63 has two ends 65 and 67 that are crossed over the top of the foot and then crossed under the foot and, by simultaneously pulling the strap 63 upward with the finger loops 69 and attaching to both medial 23 and lateral 21 sides of sock 11, the strap 63 prevents eversion and inversion. A particular advantage of strap 63 is the ability to remedy and prevent "high" ankle sprains.

Figure 6:
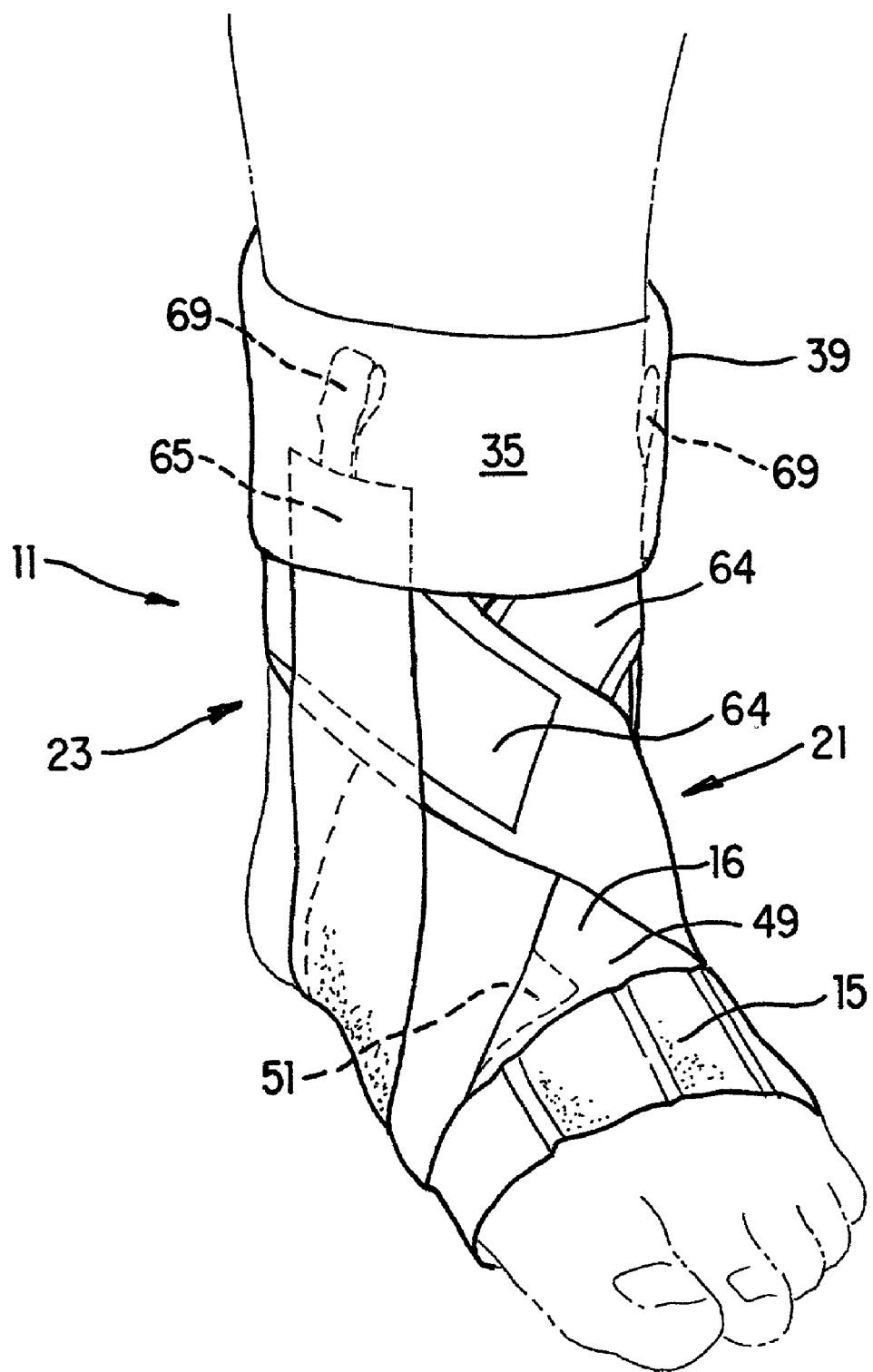
FIG. 6 is a right side perspective view of the sock, stabilizing strap, and the stirrup strap shown in FIG. 5, wherein the stirrup strap is attached and the collar is in the "down" position.

As seen in FIG. 6, collar 35 folds to an inverted "down" position over strap ends 53, 65, and 67. This secures the various strap ends 53, 65, and 67 in place after their adjustment, by a hook and loop attachment system between the collar end 37 and its outside lateral portion 39. Thus, the collar 35 that is attached to the top of sock 11 is designed to roll over the attached strapping to secure it. This allows an easy way of securing the straps without the bulk and clumsiness of a long circumferential strap.

Notwithstanding collar 35, in an alternate preferred embodiment, a securing strap (not shown) is attached to the midsection of a strap such as stirrup strap 63. This securing strap wraps around the circumference of the ankle at the upper portion of the sock 11 and attaches to itself by way of hook and loop fasteners. This strap, like the collar 35, secures all of the straps in place.

It is to be understood that to those skilled in the art that while certain embodiments of the present invention have been described and shown herein, additions, deletions, substitutions, modifications and improvements may be made without departing from the scope of the invention. For example, various hook and loop fasteners have been described. One of ordinary skill in the art would readily understand that the position of hook members and loop members of the preferred embodiments may be readily reversed without impairing the function of the present invention.

The invention is therefore not to be limited to the embodiments described and illustrated herein, but is to be determined solely from the appended claims.

I claim:

1. An ankle control system, comprising: a form-fitting sock having opposing medial and lateral sides, a foot portion having an arch portion, and an ankle portion having a vertical Achilles tendon portion; a first semi-rigid support member connected to the sock and having at least one slot providing flexibility to contour over an ankle as pressure is exerted on the support member; a lever motion stabilizing strap having a first end removably attachable to the foot portion of the sock, the stabilizing strap being wrapable around the foot portion to securely attach to the first end, and having a second end adjustably attachable to one of the lateral and medial sides; and a stirrup strap adjustably attachable to the sock along the vertical portion and having a first end sequentially wrapable from the vertical portion, around a first side, over the arch portion to an opposing second side, and under the foot portion to allow adjustable attachment to the sock on the first side.

2. The ankle control system of claim 1 wherein the stirrup strap has a second end sequentially wrapable from the vertical portion, around the second side, over the arch portion to the first side, and under the foot portion to allow adjustable attachment to the second side.

3. The ankle control system of claim 1 further comprising an elastic collar securing the first end of the stirrup strap and second end of the stabilizing strap to the sock.

4. The ankle control system of claim 1 wherein the sock comprises a laminate material no greater than about 0.025" to 0.045" thickness and comprising a polyurethane membrane no greater than about 0.001" thickness and a stretchable material covering said membrane, said material, in a stretched state, having the property of low active compressibility force and strong passive resistance to expansion substantially greater than the compressibility force.

5. The ankle control system of claim 1 wherein the lever motion stabilizing strap and the stirrup strap are attachable to the sock by a hook and loop material.

6. The ankle control system of claim 1 wherein the first end of the stabilizing strap comprises either hook or loop material on one side for attachment to the sock member, and either hook or loop material on a second side for attachment to a mid-portion of the stabilizing strap once the strap is wrapped around the foot portion.

7. The ankle control system of claim 1 wherein the at least one slot is open-ended.

8. The ankle control system of claim 1 wherein the first end of the stabilizing strap is tapered.

9. The ankle control system of claim 2 wherein the stirrup strap comprises at least one pull-loop.

10. The ankle control system of claim 8 wherein the stabilizing strap comprises at least one pull-loop.

11. The ankle control system of claim 1, further comprising a second semi-rigid support member connected to the sock and having at least one slot providing flexibility to contour over an ankle as pressure is exerted on the support member, wherein the first semi-rigid support member is connected to one side of the sock and the second support member is connected to the other side of the sock.

12. The ankle control system of claim 11, wherein the first and second support members are disposed at an angle toward the vertical Achilles tendon portion.

13. The ankle control system of claim 12, wherein the first and second support members each comprise a plurality of slots.

14. The ankle control system of claim 1, wherein the stabilizing strap has the second end adjustably attachable to the lateral side.

15. The ankle control system of claim 1, wherein the stabilizing strap has the second end adjustably attachable to the medial side.

16. The ankle control system of claim 1, wherein the first end of the stirrup strap is sequentially wrapable from the vertical portion, around the medial side, over the arch portion to the opposing lateral side portion, and under the foot portion to allow adjustable attachment to the sock on the medial side.

17. The ankle control system of claim 14, wherein the first end of the stirrup strap is sequentially wrapable from the vertical portion, around the medial side, over the arch portion to the opposing lateral side portion, and under the foot portion to allow adjustable attachment to the sock on the medial side.

18. A method of controlling an ankle, comprising the steps of: providing (1) a form-fitting sock having opposing medial and lateral sides, a foot portion having an arch portion, and an ankle portion having a vertical Achilles heel portion, (2) a first semi-rigid support member connected to the sock and having at least one slot providing flexibility to contour over an ankle as pressure is exerted on the support member, (3) a lever motion stabilizing strap, and (4) a stirrup strap; fitting the sock onto a foot; attaching a first end of the lever motion stabilizing strap to the foot portion of the sock, wrapping the stabilizing strap around the foot portion to securely attach an intermediate portion of the stabilizing strap to the first end of the stabilizing strap, and adjustably attaching a second end of the stabilizing strap to the lateral side of the form fitting sock; and adjustably attaching a stirrup strap to the sock along the vertical portion and sequentially wrapping a first end of the stirrup strap from the vertical portion, around the medial side, over the arch portion to the opposing lateral side portion, and under the foot portion, and adjustably attaching the first end to the sock on the medial side.

19. The method of claim 18, further comprising the step of: sequentially wrapping a second end of the stirrup strap from the vertical portion, around the lateral side, over the arch portion to the opposing medial side portion, and under the foot portion, and adjustably attaching the first end to the sock on the lateral side.

20. The method of claim 18, wherein the first support member comprises a plurality of slots.

21. The method of claim 18, wherein said step of providing comprises providing a second semi-rigid support member connected to the sock and having at least one slot providing flexibility to contour over an ankle as pressure is exerted on the support member, wherein the first support member is connected to the lateral side of the sock, and the second support member is connected to the medial side of the sock.

* * * * *